(12) United States Patent
Felding

(10) Patent No.: US 10,383,771 B2
(45) Date of Patent: Aug. 20, 2019

(54) SYSTEM FOR REDUCED SCARRING OF WOUNDS

(71) Applicant: Hyposkin ApS, Holstebro (DK)

(72) Inventor: Jens Ulrik Felding, Holstebro (DK)

(73) Assignee: Hyposkin ApS, Holstebro (DK)

( * ) Notice: Subject to any disclaimer, the term of this patent is extended or adjusted under 35 U.S.C. 154(b) by 1157 days.

(21) Appl. No.: 14/361,267

(22) PCT Filed: Nov. 28, 2012

(86) PCT No.: PCT/EP2012/073874
§ 371 (c)(1),
(2) Date: May 28, 2014

(87) PCT Pub. No.: WO2013/079554
PCT Pub. Date: Jun. 6, 2013

(65) Prior Publication Data
US 2014/0336564 A1 Nov. 13, 2014

Related U.S. Application Data

(60) Provisional application No. 61/564,162, filed on Nov. 28, 2011.

(30) Foreign Application Priority Data

Nov. 28, 2011 (DK) .................................. 2011 70655

(51) Int. Cl.
*A61M 35/00* (2006.01)
*A61F 13/00* (2006.01)
(Continued)

(52) U.S. Cl.
CPC .................. *A61F 13/00068* (2013.01); *A61F 2013/00246* (2013.01); *A61F 2013/00314* (2013.01)

(58) Field of Classification Search
CPC ........ A61M 35/00; A61M 1/00; A61M 27/00; A61F 13/00; A61F 13/02
See application file for complete search history.

(56) References Cited

U.S. PATENT DOCUMENTS 4,224,941 A 9/1980 Stivala
4,875,473 A 10/1989 Alvarez
(Continued)

FOREIGN PATENT DOCUMENTS

EP 1092404 A1 4/2001
WO 2009/151380 A1 12/2009
(Continued)

OTHER PUBLICATIONS

International Search Report cited by the European Patent Office in International Patent Application No. PCT/EP2012/073874 (dated Jan. 30, 2013).

(Continued)

*Primary Examiner* — Tatyana Zalukaeva
*Assistant Examiner* — Ilya Y Treyger
(74) *Attorney, Agent, or Firm* — Michael Best & Friedrich LLP

(57) ABSTRACT

A system for reduced scarring of wounds; said system comprising: means (1) for creating an enclosed volume (3) over a wound site (2). The system further comprises: means (6, 10, 11, 12) for actively reducing the oxygen concentration within the enclosed volume at the surface of the wound to a first oxygen concentration level while maintaining an environment within the enclosed volume which is healthy for wound healing, means (4, 5, 6, 7, 8, 9, 10, 11, 12, 13, 14) for ensuring that the oxygen concentration of the gas composition of the gas within the enclosed volume at the surface of the wound is maintained below a second oxygen concentration level and above a third oxygen concentration level, (Continued)

and where said system is arranged such that said first, second and third oxygen concentration levels are between 1 and 16 volume percent.

14 Claims, 5 Drawing Sheets

(51) Int. Cl.
*A61M 1/00* (2006.01)
*A61M 27/00* (2006.01)
*A61F 13/02* (2006.01)

(56) References Cited

U.S. PATENT DOCUMENTS

| | | |
|---|---|---|
| 4,969,881 A | 11/1990 | Viesturs |
| 5,788,682 A | 8/1998 | Maget |
| 5,855,570 A | 1/1999 | Scherson et al. |
| 8,480,610 B1 * | 7/2013 | Hill ................. A61F 11/002 604/8 |
| 2006/0235358 A1 | 10/2006 | Azocar |

FOREIGN PATENT DOCUMENTS

| | | |
|---|---|---|
| WO | 2010/047732 A1 | 4/2010 |
| WO | 2013/079554 A1 | 6/2013 |

OTHER PUBLICATIONS

Written Opinion mailed in International Patent Application No. PCT/EP2012/073874 (dated Jan. 30, 2013).

International Preliminary Report on Patentability mailed in International Patent Application No. PCT/EP2012/073874 (dated Jun. 3, 2014).

* cited by examiner

SYSTEM FOR REDUCED SCARRING OF WOUNDS

CROSS-REFERENCE TO RELATED APPLICATIONS

This is a U.S. national stage entry of International Patent Application No. PCT/EP2012/073874, filed on Nov. 28, 2012, which claims priority to Denmark Patent Application No. PA 2011 70655, filed on Nov. 28, 2011, and U.S. Patent Application No. 61/564,162, filed on Nov. 28, 2011, the entire contents of all of which are fully incorporated herein by reference.

The current invention relates to a system for reduced scarring of wounds; said system comprising means for creating an enclosed volume over a wound. The current invention also relates to a method to reduce the scarring of wounds.

As is well known in the art, when wounds in human/animal tissue heal, they often leave scars which are unsightly and/or disturb the normal functioning of the human/animal body.

Two non-limiting examples of wounds and the undesired effects of resulting scars are:

1. Surgical removal of deformities on the human body. After removing the deformity (for example a wart) from the skin of the human, the skin of the human heals, but an unsightly scar could be left. Depending on the location of the scar, this could be a serious cosmetic problem for the patient.
2. Ear surgery. Many children have problems with recurring inner ear infections. One solution is to surgically insert a drain in the eardrum which allows liquid from the middle ear to escape the ear through the drain placed in the eardrum. In some cases, undesired scars are formed on the inner side of the eardrum as a cause of this procedure. Such a scar can reduce the hearing ability of the patient for the rest of his or her life.

As will be known to the person skilled in the art, there are numerous other forms of wounds which may form undesired scars. Reducing the formation of scars during the healing of wounds is therefore of great interest.

In the current specification, the phrase "reduced scarring" should be understood as controlling the generation of granulation tissue and collagen during the wound healing process such that an excess of granulation tissue and collagen is reduced or not formed. Reducing the formation of excess granulation tissue and collagen will reduce the risk of hypertrophic scars, thereby also reducing the risk for scars developing into Keloid scars.

Furthermore, the phrase "means for creating an enclosed volume" should be understood in this specification as means which allows the establishment of a controlled gas environment over the wound. In most cases this will be a form of bandage system which seals against the skin of the patient while providing an essentially fluid tight barrier (where the term "fluid" can comprise both liquids and gasses) between the surface of the wound and the external environment. Many different embodiments of suitable systems for creating an enclosed volume are known in the art and details of possible solutions are therefore not provided in this specification.

It should be noted that according to the current specification the phrase "essentially fluid tight" should be understood as being so fluid tight that the gas environment inside the barrier can be effectively controlled with the controller provided. As should be clear to the person skilled in the art, the demand on the barrier's "fluid tightness" will therefore be dependent on the actual controller provided. For example, in an embodiment where there is a high flow rate of control gas through the enclosed volume, the demands to the fluid tightness of the barrier could be quite low whereas in an embodiment where there is a low flow rate of control gas, the barrier should be more fluid tight. In certain cases, a barrier which allows a certain inflow of oxygen through the barrier might even be desired.

DESCRIPTION OF RELATED ART

It is commonly accepted in the medical community that in order to improve the healing of wounds, it is important that the wound is exposed to Oxygen. There are therefore many forms of systems which apply extra oxygen to wounds. This is typically called hyperoxic therapy. However, the exact effects of oxygen are not known precisely. In fact there are studies which show that the removal of oxygen helps in wound healing. This is typically called hypoxic therapy.

In general, the prior art related to oxygen therapy in wound healing can be split into three different kinds of dressings:

1. Occlusive dressings. These dressings create an enclosed volume around the wound. No gas can enter the dressing and no gas can exit the dressing. Therefore, as the oxygen trapped under the dressing is consumed, the partial pressure of Oxygen under the dressing will slowly be reduced. Examples of such dressings are U.S. Pat. No. 4,875,473 and WO2009151380A1.
2. Vacuum dressings. These dressings actively apply a vacuum to the wound thereby reducing the partial pressure of Oxygen to very low levels under the dressing. Furthermore, the oxygen concentration of the gas remains unchanged in a vacuum dressing when vacuum is applied since the total pressure is reduced, but the gas composition is not actively changed.
3. Controlled environment dressings. These dressings attempt to actively control the environment around the wound. These dressings either create oxygen rich environments around the wound (U.S. Pat. Nos. 4,224,941, 4,969,881, WO2010047732A1, U.S. Pat. No. 5,788,682) or remove all oxygen (EP1092404A1, US2006235358A1).

SUMMARY OF THE INVENTION

It is a first aspect of the present invention to provide a system which can reduce the scarring of a wound during the wound healing process.

This aspect is provided in part by a system according to the introductory paragraph which further comprises means for actively reducing the oxygen concentration within the enclosed volume at the surface of the wound to a first oxygen concentration level while maintaining an environment within the enclosed volume which is healthy for wound healing, means for ensuring that the oxygen concentration of the gas composition of the gas within the enclosed volume at the surface of the wound is maintained below a second oxygen concentration level and above a third oxygen concentration level and where said system is arranged such that said first, second and third oxygen concentration levels are between 1 and 16 volume percent. In general the third oxygen concentration level will be lower than the second oxygen concentration level.

It should be noted that the term "oxygen concentration" should be understood in this specification as the volume percent of oxygen of the total gas. For example, the oxygen concentration as understood by the current specification in normal air is 21 volume percent.

The inventor of the current invention has discovered that by reducing, but not completely eliminating, the Oxygen concentration at the exterior of a wound, the wounds heal with much less scarring.

Under normal atmospheric conditions, the partial pressure of Oxygen in venous blood is around 40 mmHG whereas the partial pressure of Oxygen in the air of the earth's environment is around 160 mmHG. Under normal atmospheric conditions the current invention is therefore to reduce the partial pressure of Oxygen around the exterior surface of the wound to levels which are near to the partial pressure of oxygen normally found in the body, ie near to the partial pressure of oxygen in venous blood. The exact theory behind the reduced scarring is still unsure. One unconfirmed and non-binding theory could be that a high partial pressure of oxygen at the wound site can together with bacteria contamination at the wound lead to an overproduction of oxygen free radicals, for example $O2^-$, $H2O2$ and $OH^-$. The Oxygen free radicals prolong the healing process and cause scar generation via increased granulation. One factor which supports this theory is that Keloid scars contain large amounts of the above named oxygen free radicals. By reducing the partial pressure of oxygen at the wound the production of oxygen free radicals will be reduced. It should however, be noted that the inventor does not wish to be bound by this potential theory.

It should also be noted that the above discussion refers to atmospheric conditions. However, at sub atmospheric conditions, for example under conditions experienced in vacuum wound therapy, the total pressure of the gas in the enclosed volume will be less than 760 mmHg. The current claim set has therefore defined the invention in that the oxygen concentration of the gas in the enclosed volume is reduced to a first level between 1 and 16 volume percent and then maintained below a second level between 1 and 16 volume percent and above a third level between 1 and 16 volume percent. According to this restriction, if the total pressure inside the enclosed volume is 1 atm, then the partial pressure of oxygen will be reduced to a first level which is between 7.6 mmHg and 121.6 mmHg and then maintained below a second level between 7.6 mmHg and 121.6 mmHg and above a third level between 7.6 mmHg and 121.6 mmHg. In the case where the total pressure in the enclosed volume is 0.1 atm, the range of the partial pressure of oxygen will be between 0.76 mmHg and 12.16 mmHg.

However, in another invention which could be the basis for a divisional application, a system could be provided which actively reduces the partial pressure of Oxygen (PO2) in the enclosed volume to a first PO2 level and then ensures that the partial pressure of Oxygen in the enclosed volume is maintained below a second PO2 level, said first and second PO2 levels being between 10 and 120 mmHg, between 10 and 80 mmHg, between 20 and 80 mmHg, between 20 and 60 mmHg or between 30 and 60 mmHg. It should be noted that in this embodiment, the partial pressure of oxygen would be the same no matter what the absolute gas pressure in the enclosed volume is. This is in contrast to the embodiment of the current claims where the partial pressure of oxygen in the enclosed volume would change depending on the absolute gas pressure in the enclosed volume. The embodiments and dependent claims provided below related to the first invention could be modified to this other invention. For example, a sensor for measuring the partial pressure of oxygen could be provided instead of a sensor for measuring the oxygen concentration as currently specified in the claims.

It should furthermore be noted that currently available vacuum therapy systems can also be said to actively reduce the partial pressure of oxygen and maintain it below a certain level indirectly by reducing the total gas pressure inside the enclosed volume, however, it cannot be said that these known vacuum systems directly control the partial pressure of oxygen, rather they indirectly control the PO2 without actually seeking to do so.

In another invention which could be the basis for a divisional application, a system could be provided which actively reduces the oxygen concentration in the enclosed volume to essentially zero and then ensures that the oxygen concentration remains at essentially zero while maintaining atmospheric pressure inside the enclosed volume. In this way, a normal bandage system can be used without the need for vacuum proof bandages, while at the same time maintaining the low oxygen concentrations.

It should be noted that "within the enclosed volume at the surface of the wound" is understood in this specification as specifying that it is the surface of the wound which is of interest, not necessarily the rest of the enclosed volume. For example, if an enclosed volume is provided where there are several different oxygen concentration levels at different points in the enclosed volume, then the points of interest for the current specification are the points at the surface of the wound since it is the oxygen concentration of the gas which interacts with the wound itself which is of interest. Furthermore it should be noted that, the phrase "means for actively reducing the oxygen concentration at the surface of the wound" should not be interpreted in that the means for reducing need to be located at the surface of the wound. The means could be located anywhere, as long as the oxygen concentration at the surface of the wound is reduced by the means. The same is true for any potential means for increasing the oxygen concentration.

According to this specification the phrase "means for actively reducing the oxygen concentration within the enclosed volume" should be understood as means which are able to reduce the oxygen concentration in the enclosed volume in a manner which is faster than the natural reduction of oxygen concentration in the enclosed volume of an occlusive dressing. In one example embodiment, the means for actively reducing the oxygen concentration within the enclosed volume can reduce the oxygen concentration from ambient levels to said first oxygen concentration level within 2 hours. In other embodiments, the reduction can occur within 1 hour, within 30 minutes, within 10 minutes, within 5 minutes, within 1 minute. It should also be noted that means to actively reduce the oxygen concentration within the enclosed volume to a first level, should be understood in this specification as means which actively seek to reduce and to establish the oxygen concentration in the enclosed volume around the first level. Systems which seek to reduce the oxygen concentration level to a level below or above the first level, but which would go through the first level, should not be considered as falling within the scope of the claims. For example, a system which seeks to reduce the oxygen concentration level to zero, would automatically cause the oxygen concentration to go through the range defined in the claims, however, it would not be a system which seeks to reduce the oxygen concentration to a first level as defined in the claims.

The phrase "means for ensuring that the oxygen concentration of the gas composition of the gas within the enclosed volume at the surface of the wound is maintained below a second oxygen concentration level and above a third oxygen concentration level" should be understood as a means which ensures that the oxygen concentration within the enclosed volume is held below a certain level and above another level over a certain amount of time.

These means could either be automatic via a sensor/controller system, or it could be manual via manual interaction by a patient/care-person or it could be passive in that the materials/form etc of the system are chosen such that the desired oxygen concentration level is maintained below the desired level over time. In one embodiment, the time over which the desired oxygen concentration level is maintained is 1 hour, in another embodiment the time is 2 hours, in another embodiment the time is 6 hours, in another embodiment the time is 12 hours, in another embodiment the time is 24 hours and in another embodiment the time is 48 hours. It should also be noted that the means for reducing and the means for maintaining could be the same physical means. For example a controller with an oxygen poor gas source, could be used both to initially reduce the oxygen concentration and then afterwards maintain the oxygen concentrations as desired.

Furthermore, it should be noted that the system could be arranged such that the second oxygen concentration level changes over time such that the oxygen concentration is maintained below one oxygen concentration level for a first amount of time, followed by maintaining the oxygen concentration below another oxygen concentration level for a second amount of time. Further times and values could be imagined.

The phrase "while maintaining an environment within the enclosed volume which is healthy for wound healing" should be understood in this specification as requiring a system which does not generate an environment at the wound surface which contains an excess of fluids (gasses, particles or liquids) which negatively affect the wound healing process. For example, there are chemical devices which can reduce the partial pressure of oxygen via chemical processes which simultaneously introduce chemicals such as H2 or OH to the wound site. Such chemicals introduced in excess into the wound site would not be considered healthy for wound healing. The limitation imposed by this requirement should be interpreted in a case by case manner.

It should furthermore be noted that according to the current invention, it is not desired to remove all the Oxygen from the wound surface. The invention is therefore defined in that the Oxygen concentration at the wound surface needs to be reduced to a first value and then maintained below a second level and above a third level.

The first value is in a first embodiment defined to be chosen from a range comprising oxygen concentrations between 1 and 16 volume percent. In another embodiment, the range is between 1 and 13 volume percent. In another embodiment, the range is between 1 and 10 volume percent. In another embodiment, the range is between 2 and 10 volume percent. In another embodiment, the range is between 2 and 8 volume percent. In another embodiment, the range is between 3 and 8 volume percent. In another embodiment, the range is between 4 and 6 volume percent.

The second value is in a first embodiment defined to be chosen from a range comprising oxygen concentrations between 1 and 16 volume percent. In another embodiment, the range is between 1 and 14 volume percent. In another embodiment, the range is between 1 and 12 volume percent. In another embodiment, the range is between 2 and 10 volume percent. In another embodiment, the range is between 3 and 10 volume percent. In another embodiment, the range is between 3 and 8 volume percent. In another embodiment, the range is between 4 and 7 volume percent.

In one embodiment, the third oxygen concentration level could be chosen from a range of between 1 and 10 volume percent, a range of between 1 and 8 volume percent, a range of between 1 and 6 volume percent, a range of between 1 and 4 volume percent, a range of between 2 and 4 volume percent or a range of between 2 and 3 volume percent.

It should also be mentioned that there could be systems in the prior art which have means which could reduce the oxygen concentration at the wound surface, but it is currently the inventor's and the applicant's impression that there are no systems currently disclosed which are arranged to actively reduce the oxygen concentration at the wound surface to the values described in this specification and then maintain the oxygen concentration as specified in this specification. In general, it could be said that the system according to the invention as defined in the claims seeks to first establish and then maintain an environment around the wound site where the oxygen concentration is within a range defined by the second and third oxygen concentration levels.

In one embodiment, the system could be arranged to ensure that the environment within the enclosed volume could approximate venous gas pressure and composition, at least with respect to the oxygen concentration. In this respect, the oxygen concentration could, in one embodiment, first be reduced to 5.2 volume percent and then maintained at 5.2 volume percent.

In another embodiment, the system could be arranged such that the gas composition within the enclosed volume comprises an oxygen concentration between 2 and 9 volume percent, a carbon dioxide concentration between 3 and 9 volume percent, a water vapour concentration between 2 and 20 volume percent and a nitrogen concentration between 40 and 90 volume percent.

The system could further comprise a sensor for measuring the oxygen concentration in the enclosed volume. The sensor could be arranged in different manners as will be known to the person skilled in the art of sensors. In a common situation, the sensor could measure the oxygen concentration directly and convert this to an electronic signal for feedback to, for example, a controller. In another embodiment the sensor could take the form of an indirect measurement, where the oxygen concentration could, for example, be translated to a colour via a pressure sensitive film and the colour read manually by a user or automatically by a colour sensor. The term sensor should therefore be read broadly.

In one embodiment of the system the means for actively reducing the oxygen concentration within the enclosed volume could comprise an inlet for introducing gas into the enclosed volume and an outlet for allowing gas to leave the enclosed volume. In this way, the system is able to control the pressure within the volume. In some prior art types of bandage systems a vacuum is generated if oxygen is removed. This can be beneficial in certain circumstances, but is undesired in others. By providing both an inlet and an outlet in the enclosed volume, gas can be easily introduced and removed from the volume. It should be mentioned that in certain embodiments, the inlet and outlet will be combined into a single opening in the enclosed housing where a control element connected to the opening either injects or sucks out gas from the enclosed volume.

In one embodiment, the outlet could be a pressure relief valve. This provides a simple and robust solution to controlling the pressure inside the enclosed volume.

In one embodiment of the system, an inlet and an outlet could be provided one on either side of the wound, so that gas which flows from the inlet to the outlet crosses the wound.

In one embodiment, the means for actively reducing the oxygen concentration within the enclosed volume could further comprise an oxygen poor gas source comprising a gas having less than 15 volume percent oxygen. In another embodiment, the gas source comprises a gas having less than 10 volume percent oxygen, less than 8 volume percent or less than 5 volume percent oxygen. Two non-limiting examples are 1) a canister of pressurized gas and 2) an unpressurized canister of gas connected to a pump.

In one embodiment, the means for ensuring that the oxygen concentration of the gas composition of the gas within the enclosed volume at the surface of the wound is maintained below a second oxygen concentration level and above a third oxygen concentration level could further comprise a control element which controls the composition and/or pressure and/or flow of the gas introduced into the enclosed volume at the inlet based on the measurement of the sensor. In this way, the gas environment inside the enclosed volume can be controlled as desired.

In one embodiment the means for ensuring that the oxygen concentration of the gas composition of the gas within the enclosed volume at the surface of the wound is maintained above a third oxygen concentration level could comprise an oxygen rich gas source comprising a gas having more than 20 volume percent oxygen. This would allow the oxygen concentration of the gas composition in the enclosed volume to be actively increased if desired. The gas having more than 20 volume percent oxygen could in one embodiment be normal air, which has ~21% volume percent oxygen. "Normal air" as used in this specification should be understood as being the air which is available in the environment outside the enclosed volume. The exact composition/pressure of "Normal air" will change depending on the environment. In certain cases, the normal air could be filtered before being introduced into the enclosed volume.

It should also be noted that in typical wound dressings, if the oxygen concentration is reduced to a low level after applying the dressing, the oxygen concentration will slowly rise over time. Therefore, in most cases, it is not necessary to have active means to ensure that the oxygen concentration remains above the third oxygen concentration level. This is usually only necessary in situations where the system comprises an oxygen consumer, which over time removes oxygen from the enclosed volume. In this situation, it might be necessary to actively add oxygen to the enclosed volume over time.

The invention also relates to a method for reducing the scarring of a wound during the wound healing process. In one embodiment, the method comprises the steps of establishing an enclosed volume around the wound, actively reducing the oxygen concentration in the enclosed volume at the surface of the wound to a first oxygen concentration level which is between 1 and 16 volume percent and ensuring that the oxygen concentration in the enclosed volume at the surface of the wound is maintained below a second oxygen concentration level which is between 1 and 16 volume percent and above a third oxygen concentration level which is between 1 and 16 volume percent. Other levels and ranges of oxygen concentrations as disclosed elsewhere in this specification could also be used.

In one embodiment of the method, the method could further comprise the step of measuring the oxygen concentration in the enclosed volume and controlling the introduction of a gas into the enclosed volume to actively control the oxygen concentration within the enclosed volume.

The invention also relates to the use of a system as disclosed herein for the treatment of a wound with reduced scarring.

The invention also relates to a product providing a system according to any one of the embodiments disclosed herein for the purpose of reduced scarring during the wound healing process.

It should be emphasized that the term "comprises/comprising/comprised of" when used in this specification is taken to specify the presence of stated features, integers, steps or components but does not preclude the presence or addition of one or more other features, integers, steps, components or groups thereof.

BRIEF DESCRIPTION OF THE DRAWINGS

In the following, the invention will be described in greater detail with reference to embodiments shown by the enclosed figures. It should be emphasized that the embodiments shown are used for example purposes only and should not be used to limit the scope of the invention unnecessarily.

DETAILED DESCRIPTION OF THE EMBODIMENTS

Figure 1:
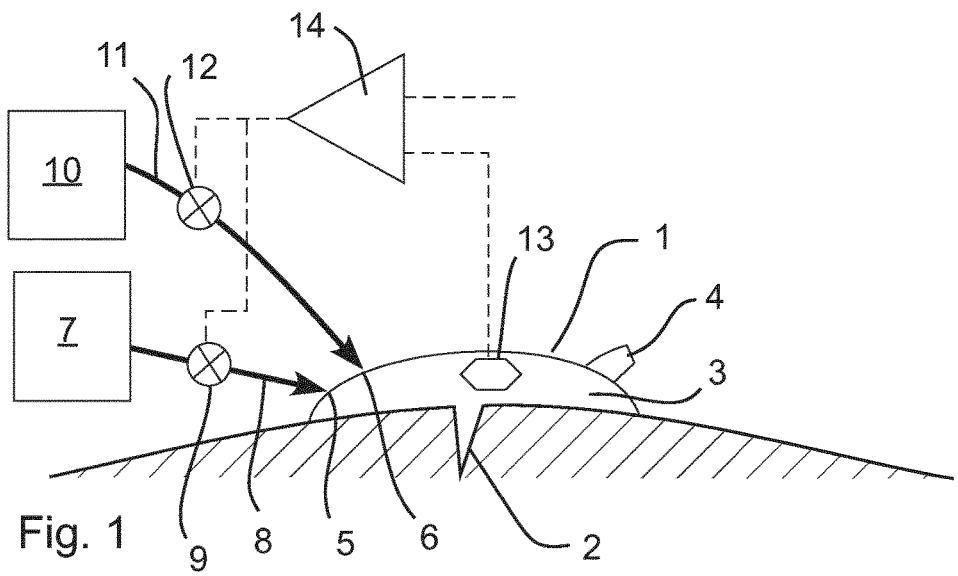
FIG. 1 shows a very schematic view of a first embodiment of a system according to the invention mounted at a wound site.

In the embodiment shown in FIG. 1, a bandage 1 is provided at a wound site 2. The bandage is provided in a form which is of the kind known in the prior art which establishes an enclosed volume 3 within the bandage and at the wound site.

The bandage is provided with a pressure relief valve 4 which is set to release pressure from inside the enclosed volume if the pressure within the enclosed volume goes over atmospheric pressure. This pressure relief valve would be considered an outlet in the terms of the claims. The bandage is further provided with two inlets 5,6. The first inlet 5 is connected to an oxygen poor gas source, in this embodiment a pressurized gas canister 7, via a hose 8 and a valve 9. When the valve 9 is opened, the gas from the gas canister 7 is introduced into the enclosed volume via the first inlet 5. In this embodiment, the oxygen poor gas canister comprises a gas comprising less than 15% oxygen by volume. For example, the oxygen poor gas canister could comprise a mixture comprising 5% Oxygen, 20% CO2 and 75% N2. The second inlet 6 is connected to an oxygen rich gas source, in this case a pressurized gas canister 10, via a hose 11 and a valve 12. In this embodiment, the oxygen rich gas canister comprises a gas comprising more than 15% oxygen by volume, for example 30% oxygen, 40% CO2 and 30% N2. In another embodiment, the oxygen rich gas canister could comprise compressed normal air. In another embodiment, the oxygen rich gas source could comprise a pump which pumps normal air into the enclosed volume.

The bandage further comprises a sensor 13 for measuring the Oxygen concentration in the enclosed volume 2. This could for example be a compound sensor comprising two separate sensors one of which measures the partial pressure of oxygen and the other measuring the total pressure. The signal from the sensor 13 is fed to a controller 14 which controls the valves 9,12. If the oxygen concentration within the enclosed volume is too low, then the valve 12 connected to the oxygen rich gas canister is opened, allowing oxygen rich gas to enter the enclosed volume. Due to the pressure relief valve 4, the total gas pressure within the enclosed volume will not exceed safe limits. If the oxygen concentration within the enclosed volume is too high, then the controller will open the valve 9 connected to the oxygen poor gas canister and allow oxygen poor gas to enter the enclosed volume. In this way, a precise control of the oxygen concentration in the enclosed volume can be achieved.

When using the embodiment of the system shown in FIG. 1, the bandage would be applied to the patient to establish an enclosed volume around the wound site. The system would then be programmed to establish the desired oxygen concentration in the enclosed volume. In one example, the system would be programmed such that the system maintains the Oxygen concentration at around 5.2 volume %. In the terms of the claims, the system would first reduce the Oxygen concentration to 5.2 volume % by flushing the enclosed volume with gas from the oxygen poor gas source. Then once the Oxygen concentration reached 5.2 volume %, then the controller would maintain the Oxygen concentration at around 5.2 volume %. As will be known to the person skilled in the art of control engineering, there will always be a slight difference between the set point and the actual concentration, therefore, in the terms of the claims, the oxygen concentration will be held between a second and third level, the second and third level being slightly higher and slightly lower respectively than 5.2 volume %. Depending on the efficiency of the controller, the range will be more or less tight around the desired set point.

Figure 2:
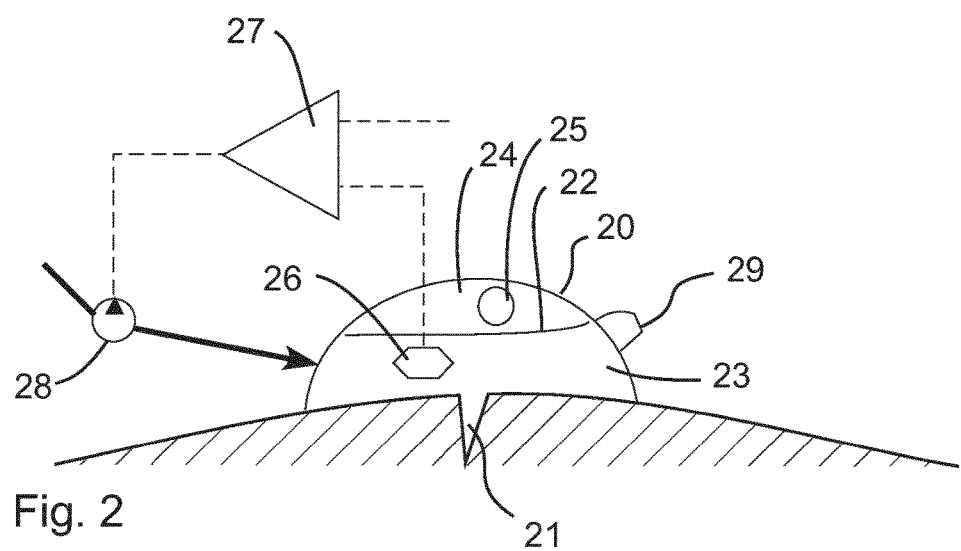
FIG. 2 shows a very schematic view of a second embodiment of a system according to the invention mounted at a wound site.

In the embodiment shown in FIG. 2, a bandage 20 is provided at the wound site 21 in a manner similar to the one of the embodiment of FIG. 1. The bandage 20 of FIG. 2 further comprises a membrane 22 which splits the enclosed volume established by the bandage into two volumes, a first enclosed volume 23 adjacent the wound site and a second enclosed volume 24 apart from the wound site. The membrane 22 is arranged to allow oxygen to flow from the first enclosed volume 23 to the second enclosed volume 24, but not vice versa.

An oxygen consumer 25 is arranged in the second enclosed volume 24. Oxygen which enters the first enclosed volume passes into the second enclosed volume 24 and is actively consumed there. The bandage also comprises a sensor 26 for measuring the oxygen concentration within the first enclosed volume 23. The sensor is connected to a controller 27 which operates a small air pump 28. When the oxygen concentration within the first enclosed area drops below a certain threshold value, the controller activates the pump, thereby pumping normal air into the first enclosed volume. As the oxygen in the normal air is consumed, new normal air is injected into the first enclosed volume. A pressure relief valve 29 is also provided to ensure that the pressure is not increased to unsafe levels. In the current embodiment, the pressure relief valve is set to a pressure slightly higher than atmospheric pressure.

In another embodiment (not shown) instead of normal air, an oxygen rich pressurized gas canister could be connected to the first enclosed volume via a valve.

Figure 3:
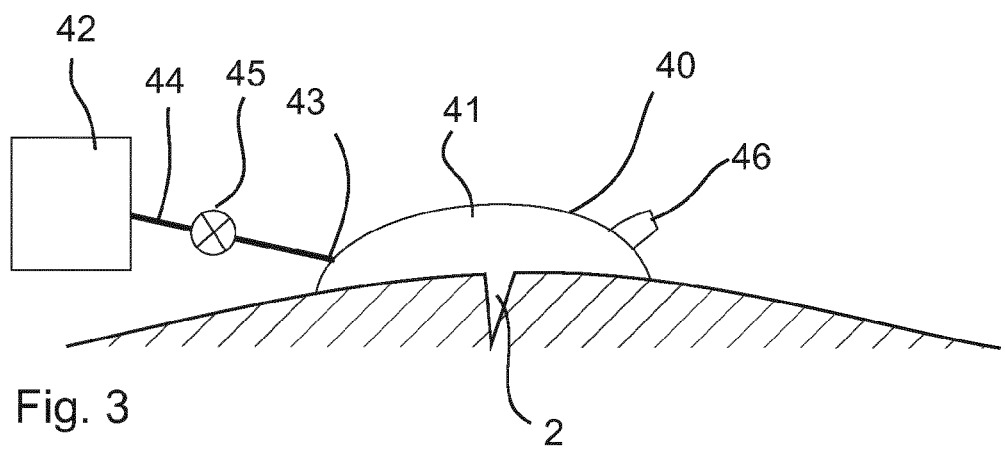
FIG. 3 shows a very schematic view of a third embodiment of a system according to the invention mounted at a wound site.

The embodiment shown in FIG. 3 comprises a bandage 40 forming an enclosed volume 41. A pressurized gas canister 42 is provided and filled with a suitable gas mixture. In one embodiment, the gas mixture comprises 4% O2, 75% N2 and 21% CO2. The gas canister is connected to an inlet 43 in the bandage via a hose 44. A valve 45 in the hose allows the flow from the gas source to be controlled. A pressure relief valve 46 in the bandage allows the gas inside the bandage to escape without causing excess pressure within the bandage. In the current embodiment, the pressure relief valve is set to slightly higher than atmospheric pressure. In this embodiment, the pressure relief valve is set to 780 mmHG.

When the bandage is first applied to the patient, the valve is opened and gas is allowed to flush the enclosed volume. Once the enclosed volume is completely flushed, the valve is closed a bit more such that a small flow of gas constantly enters the enclosed volume. The pressure relief valve ensures that the pressure inside the enclosed volume does not exceed an upper limit. In this way, the gas composition inside the enclosed volume can be controlled precisely without the need for any sensor or controller.

In another embodiment similar to the one shown in FIG. 3, an oxygen sensor could be provided in the enclosed volume. The sensor could constantly measure the oxygen concentration in the enclosed volume and a controller could control the valve 45. This would slightly increase the complexity of the system, but would allow the use of a smaller gas canister 42 and/or a longer use time without the need for exchanging canisters.

In a very simple embodiment similar to the one shown in FIG. 3, the bandage could be applied to the wound and then flushed with gas from a detachable oxygen poor gas source. The oxygen poor gas source could then be disconnected from the bandage, leaving the enclosed volume filled with gas. Depending on the oxygen concentration of the oxygen poor gas source, the permeability of the bandage and the oxygen creation/consumption due to the wound healing process, the actual oxygen concentration in the enclosed volume may rise or fall over time. If the different parameters are known or can be approximated, it should be possible to predict when the oxygen concentration will rise or fall outside of the desired range. The enclosed volume can then be flushed with gas from the detachable oxygen poor gas source or the bandage exchanged and the new bandage flushed at predetermined periods. Another option is to apply an oxygen sensor to the enclosed volume which gives a signal when the oxygen concentration goes outside of the desired range. The user could then flush the enclosed volume with the oxygen poor gas or exchange the bandage. In this embodiment, the means for actively reducing would be the oxygen poor gas source and the inlet and the means for ensuring would be the combination of the actual bandage used, the model of oxygen consumption/production and the periodic flushing/exchange of the bandage system.

Depending on the type of bandage used and the oxygen consumption/production inside the bandage system, it might not even be necessary to exchange or flush the bandage system regularly as the oxygen concentration could be maintained within the desired limits for the desired amount of time without the need for manual or automatic "maintenance".

In one embodiment, one could imagine a system for reduced scarring of wounds; said system comprising: a bandage for creating an enclosed volume over a wound site, characterized in that said system further comprises: an inlet for introducing gas into said enclosed volume, an outlet for allowing gas to leave the enclosed volume and an oxygen poor gas source whereby the oxygen poor gas source can be periodically and detachably connected to the inlet in order to flush the enclosed volume such that the oxygen concentration in the enclosed volume adjacent the wound site is between 1 and 16 volume percent.

Figure 13:
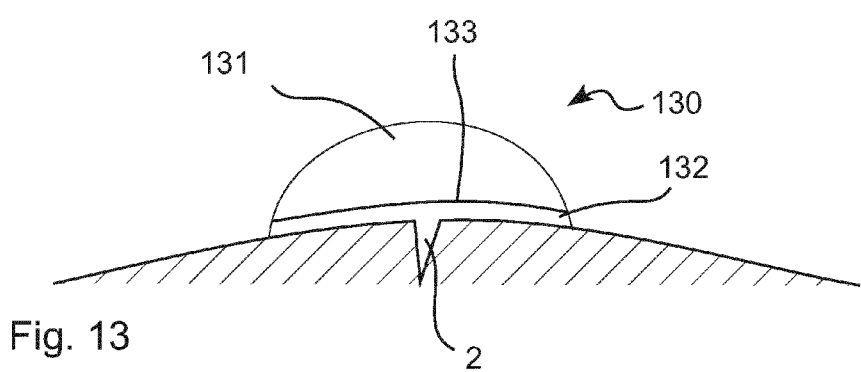
FIG. 13 shows a very simple schematic view of a simple embodiment of a system according to the current invention mounted at a wound site before activation.

In one even more simple embodiment, see FIG. 13, a bandage 130 could be imagined where the bandage comprises means for establishing an enclosed volume 132 about a wound site. The bandage furthermore comprises a control volume 131 connected to the enclosed volume but separated there from by a rupturable or removable membrane 133. The control volume 131 would be filled and sealed with a gas having a predetermined Oxygen concentration between 0 and 16 volume percent, for example 5.2 volume %. Once the bandage is applied to the patient, an enclosed volume 132 would be established around the wound site. Due to the mounting procedure and the form of the bandage, the enclosed volume would be filled with normal air. The membrane would then be ruptured or removed and the gas from the control volume could enter the enclosed volume. In this way, the gas from the control volume would mix with the gas in the enclosed volume and thereby establish an Oxygen concentration at the wound site different than normal air. Depending on the oxygen concentration in the control volume and the ratio of the size of the control volume to the enclosed volume, the oxygen concentration in the resulting enclosed volume can be determined. Over time it is expected that the Oxygen concentration would go outside of a desired range. At this time the bandage would be changed with a new bandage.

In another embodiment (not shown), a small pressure relief valve could be placed in the membrane and a small pressure relief valve could be placed in the wall of the enclosed volume which separates the enclosed volume from the outside of the bandage. An expandable element, for example expanding foam, could be placed in the control volume. Once the bandage is in place at the wound site, the expandable element could be activated, whereby the gas from the control volume would slowly be pressed into the enclosed volume by the expandable element via the pressure relief valve in the membrane. In another embodiment (not shown) instead of having an uncompressed control volume, the control volume could comprise a compressed gas source filled with an oxygen poor gas and it could be connected to the second volume via a small valve, for example a valve which permits a slow but steady flow of gas into the enclosed volume. Once the control volume is empty, the bandage or just the control volume could be changed.

Figure 4:
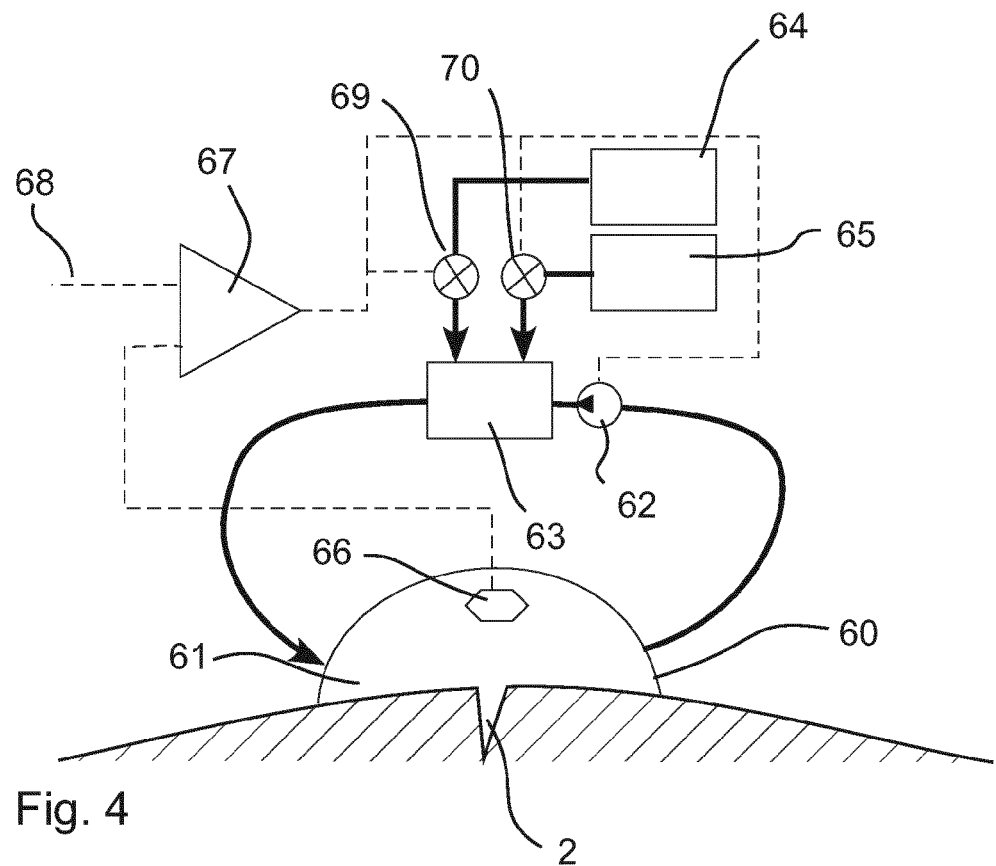
FIG. 4 shows a very schematic view of a fourth embodiment of a system according to the invention mounted at a wound site.

In the embodiment of FIG. 4, a bandage 60 is provided which again defines an enclosed volume 61 over the wound site 2. In this system, a pump 62 constantly circulates the gas inside the enclosed volume through a filter unit 63. The filter unit can blend gas from an oxygen rich gas source 64 and gas from an oxygen poor gas source 65 with the gas being circulated through the enclosed volume. In the current embodiment, the oxygen rich gas source is pure oxygen and the oxygen poor gas source is pure CO2. In another embodiment, the oxygen rich gas source could be normal compressed air or a pump which pumps normal air into the filter unit.

An oxygen sensor 66 is provided inside the enclosed volume which constantly feeds the measured oxygen concentration in the enclosed volume to a controller 67. The controller 67 compares the oxygen concentration with a desired oxygen concentration 68 and controls valves 69,70 connected to the oxygen rich and oxygen poor gas sources 64,65 respectively. By manipulating the valves 69,70 the oxygen concentration of the gas being circulated through the enclosed volume can be controlled precisely.

In the embodiment shown, the oxygen sensor 66 is provided inside the enclosed volume. However, in another embodiment, the oxygen sensor could be placed inside the filter unit itself. In this way, a self-contained filter unit could be connected to a low tech bandage via two hoses. All the electronics would then be placed in the filter unit.

It should be noted that the controller 67 mentioned in this embodiment controls the oxygen concentration to a certain specific level 68. However, different strategies for the controller could be implemented in this and other embodiments with a controller. For example, one example strategy could be to reduce the oxygen concentration to 5.2 volume percent followed by a period of no activity until the oxygen concentration went above 10 volume percent, after which the oxygen concentration was again reduced to 5.2 volume percent. Different values and ranges could be imagined.

Figure 5:
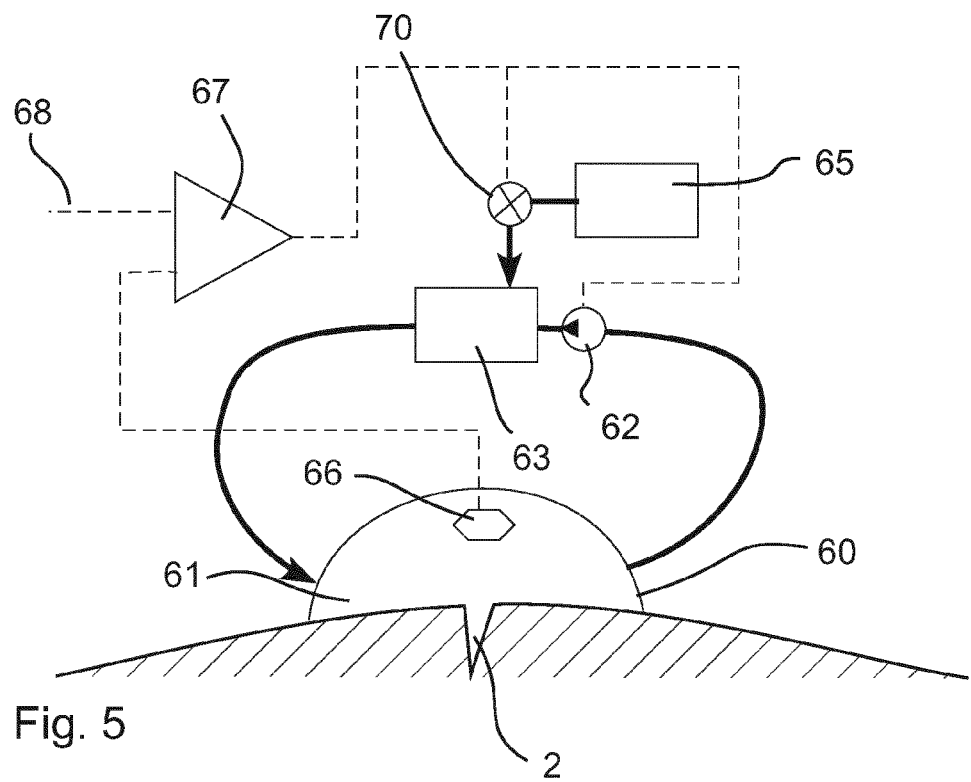
FIG. 5 shows a very schematic view of a fifth embodiment of a system according to the invention mounted at a wound site.

In FIG. 5, an embodiment is shown which is basically identical to the embodiment shown in FIG. 4, but without the oxygen rich gas source 64. In this embodiment, oxygen poor gas is fed through the enclosed volume when the oxygen concentration increases above a predefined limit. It is in this embodiment not possible to actively increase the oxygen concentration in the enclosed volume. However, depending on the permeability of the dressing 60, the oxygen concentration in the enclosed volume will naturally increase over time due to diffusion from the external environment through the dressing 60. Via the oxygen poor gas source, it will always be possible to reduce the oxygen concentration in the enclosed volume and in this way control the oxygen concentration in the enclosed volume.

Figure 6:
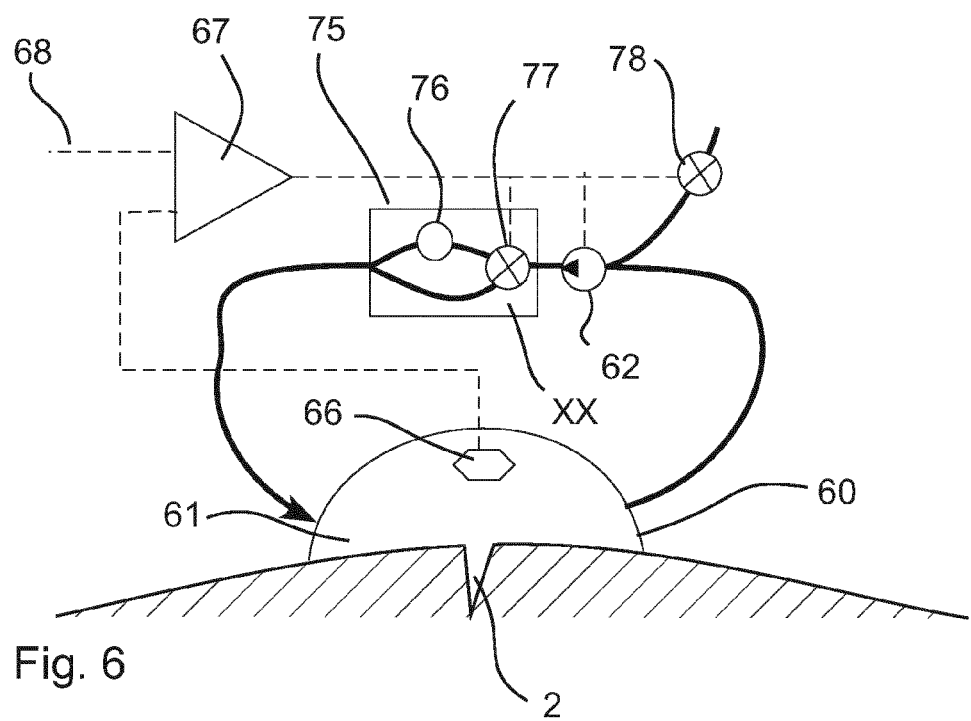
FIG. 6 shows a very schematic view of a sixth embodiment of a system according to the invention mounted at a wound site.

FIG. 6 shows another embodiment which is in certain ways similar to the embodiments of FIG. 5, and therefore shares some of the same reference numerals for similar features. In general, instead of having an oxygen poor gas source, the embodiment of FIG. 6 comprises a filter unit 75 with an oxygen consumer 76 and a Y valve 77. In general, the Y valve is set so that gas flows through the oxygen consumer 76 and thereby constantly reduces the amount of oxygen in the enclosed volume. Should the oxygen concentration in the enclosed volume attain the correct level, then the Y-valve 77 redirects the flow around the oxygen consumer so that the gas flow bypasses the oxygen consumer. In this way the oxygen in the enclosed volume is not completely consumed. If extra oxygen is needed, then a valve 78 connected to normal air is opened, allowing air to be sucked into the system. A pressure relief valve (not shown) can be incorporated into the filter unit to ensure that the gas pressure does not rise above a present amount.

One of the advantages of this embodiment is that no pressurized gas source is required and the oxygen consumer can be a cartridge which is disposable and easily replaceable. The oxygen consumer 76 can then be exchanged at regular intervals. In the case where it can be certain that the oxygen concentration in the enclosed volume rises naturally due to the permeability of the bandage and/or the physiological process occurring at the wound site, it might not even be necessary to introduce an oxygen rich gas source into the system, since it is not desired at any time to increase the oxygen concentration, only to decrease it.

Figure 7:
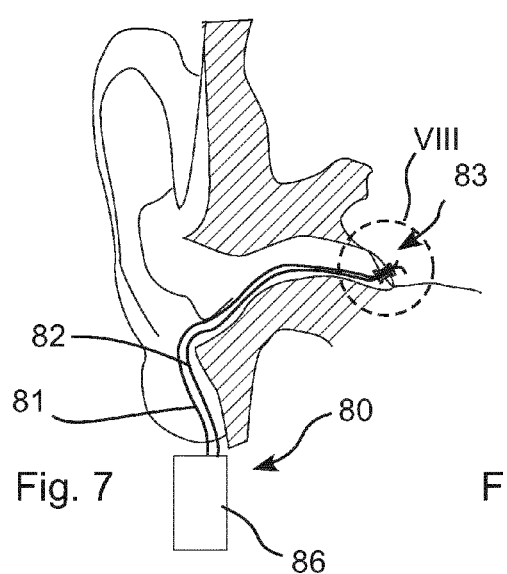
FIG. 7 shows a very schematic view of a first embodiment of a system for treating otitis according to the invention attached to an ear.
Figure 8:
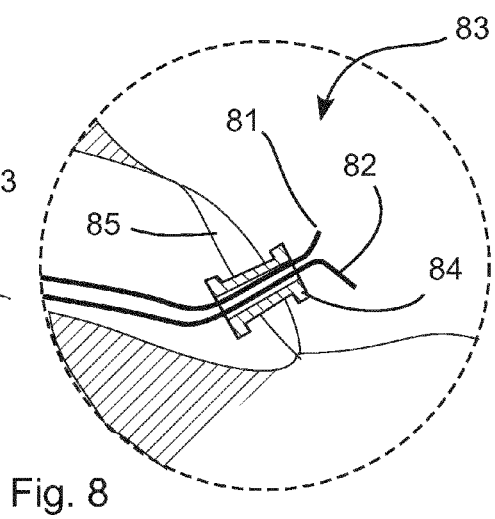
FIG. 8 shows a close-up view of the area marked VIII in FIG. 7.

In FIGS. 7 and 8 a system 80 suitable for use during the treatment of inner ear infections is shown. The system comprises two tubes 81, 82 which are inserted into the middle ear 83 via a grommet 84 which is placed through the ear drum 85 in the conventional manner. Via the first tube 81, a gas having a gas composition with an oxygen concentration of 5.2 volume percent is added to the middle ear. The second tube 82 is connected to a suction source to suck gas and liquids from the middle ear. A pressure sensor connected to the first tube 81 ensures that the pressure inside the middle ear does not rise excessively. As with the embodiment shown in FIG. 4, the two tubes could be connected to a filter unit 86 which provides both the suction and the correct gas composition. Or in another system, the gas supply and the suction could be provided by two different mechanisms. For example the gas supply could be provided in a manner similar to the embodiment of FIG. 3 while the suction source could be a simple suction source not connected to the gas supply in any way.

Figure 9:
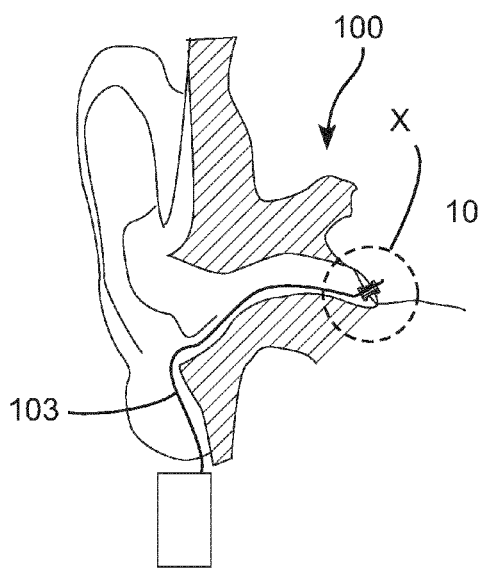
FIG. 9 shows a very schematic view of a second embodiment of a system for treating otitis according to the invention attached to an ear.
Figure 10:
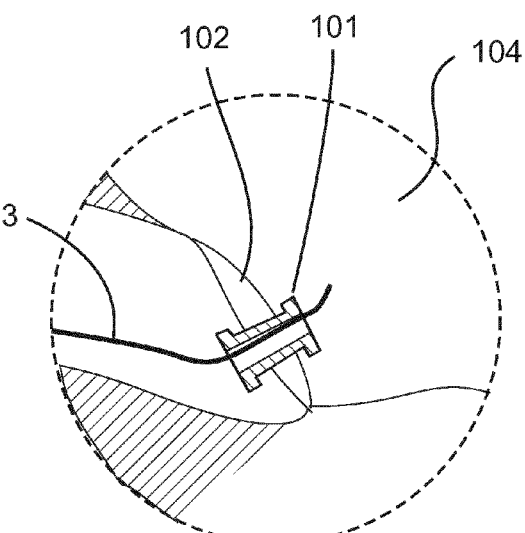
FIG. 10 shows a close-up view of the area marked X in FIG. 9.

In FIGS. 9 and 10, another system 100 for treating inner ear infections is shown. In this system a grommet 101 is again inserted into the ear drum 102 as is known in the art. A tube 103 is placed through the grommet, but the grommet and the tube are sized such that liquid and gas can still pass through the grommet. Gas having the desired oxygen concentration is then supplied to the middle ear 104 via the tube at a constant rate. As the pressure in the middle ear increases, the gas can escape via the grommet 101. The grommet and tube are sized such that the pressure inside the middle ear will always be slightly higher than the atmospheric pressure. In this way, normal air will not be able to enter the middle ear through the grommet.

Figures 11, 12:
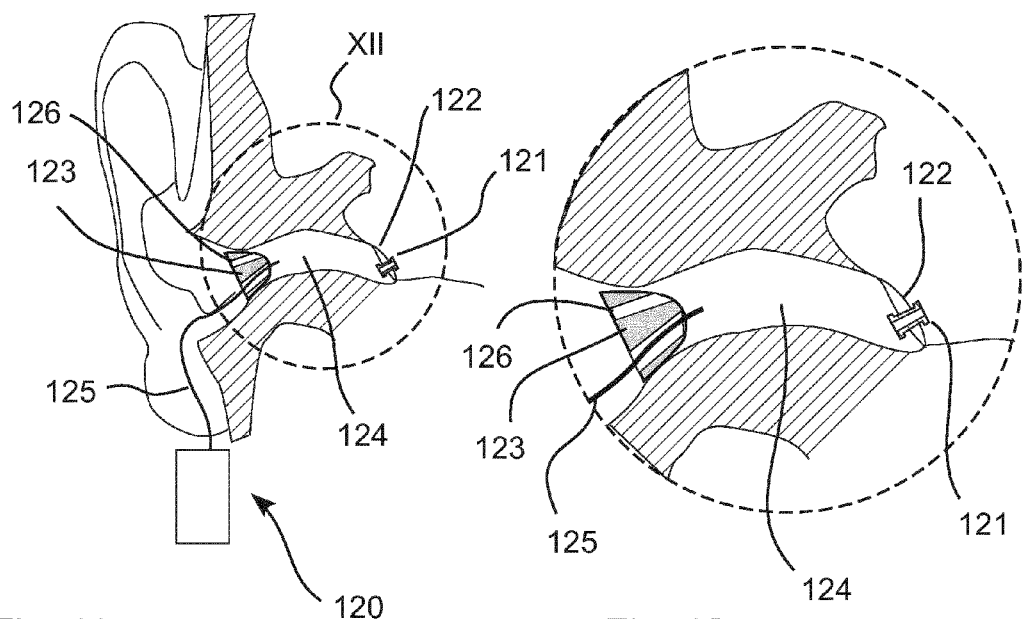
FIG. 11 shows a very schematic view of a third embodiment of a system for treating otitis according to the invention attached to an ear.
FIG. 12 shows a close-up view of the area marked XII in FIG. 11.

In FIGS. 11 and 12, a third embodiment of a system 120 is shown. In this embodiment, a grommet 121 is inserted into the ear drum 122 as is traditionally done today. An earplug 123 is then inserted into the ear to block the ear canal 124. A tube 125 is inserted through the earplug. Gas under controlled conditions is inserted into the blocked off ear canal via the tube 125. A pressure relief valve 126 built into the ear plug is provided to ensure that the gas pressure in the ear canal does not exceed safe and comfortable limits. As liquid leaks out through the grommet, the ear canal will fill up and require removal of the ear plug once in a while to remove liquid.

Other embodiments are of course possible. For example, the above embodiments have all disclosed embodiments where the pressure within the enclosed volume is at atmospheric pressure or slightly higher. It could however also be imagined that the pressure within the enclosed volume was lower than atmospheric pressure. In this way, one could combine traditional vacuum wound therapy and the oxygen therapy according to the current invention. In this case, it might be interesting to control the partial pressure of oxygen in the enclosed volume to be close to that of oxygen in venous blood.

It is to be noted that the figures and the above description have shown the example embodiments in a simple and schematic manner. The electronic and mechanical details have not been shown since the person skilled in the art should be familiar with these details and they would just unnecessarily complicate this description.

The invention claimed is:

1. A system for reduced scarring of wounds; said system comprising:
    means for creating an enclosed volume over a wound site
    means for actively reducing the oxygen concentration within the enclosed volume at the surface of the wound to a first oxygen concentration level while maintaining an environment within the enclosed volume which is healthy for wound healing,
    means for ensuring that the oxygen concentration within the enclosed volume at the surface of the wound is maintained below a second oxygen concentration level and above a third oxygen concentration level, and
    where said system is arranged such that said first, second and third oxygen concentration levels are between 1 and 16 volume percent.

2. A system according to claim 1, characterized in that said environment within the enclosed volume approximates venous gas pressure and composition, at least with respect to the oxygen concentration.

3. A system according to claim 1 characterized in that the system further comprises a sensor for measuring the oxygen concentration in the enclosed volume.

4. A system according to claim 3, characterized in that said means for actively reducing the oxygen concentration within the enclosed volume comprise an inlet for introducing gas into the enclosed volume and an outlet for allowing gas to leave the enclosed volume.

5. A system according to claim 4, characterized in that said outlet is a pressure relief valve.

6. A system according to claim 4, characterized in that the inlet and the outlet are provided on either side of the wound, so that gas which flows from the inlet to the outlet crosses the wound.

7. A system according to claim 4, characterized in that the means for actively reducing the oxygen concentration within the enclosed volume further comprises an oxygen poor gas reservoir comprising a gas having an oxygen concentration of less than 15 volume percent.

8. A system according to claim 7, characterized in that the oxygen poor gas reservoir is arranged to be detachable from the inlet.

9. A system according to claim 4, characterized in that said means for ensuring that the oxygen concentration within the enclosed volume at the surface of the wound is maintained below a second oxygen concentration level further comprises a control element which controls the composition and/or pressure and/or flow of the gas introduced into the enclosed volume at the inlet based on the measurement of the sensor.

10. A system according to claim 9, characterized in that said system is arranged for treating otitis; said system further comprising:

means for draining liquid from the middle ear.

11. A method for reducing the scarring of a wound during the wound healing process, said method comprising the steps of establishing an enclosed volume around the wound, actively reducing the oxygen concentration in the enclosed volume at the surface of the wound to a first oxygen concentration level which is between 1 and 16 volume percent and ensuring that the oxygen concentration in the enclosed volume at the surface of the wound is maintained below a second oxygen concentration level which is between 1 and 16 volume percent and above a third oxygen concentration level which is between 1 and 16 volume percent.

12. A method according to claim 11, characterized in that the method further comprises the step of measuring the oxygen concentration in the enclosed volume and controlling the introduction of a gas into the enclosed volume to actively control the oxygen concentration within the enclosed volume.

13. A method according to claim 12 characterized in that the method further comprises the steps of attaching an oxygen poor gas reservoir to the enclosed volume via an inlet into the enclosed volume, flushing the enclosed volume with the gas from the oxygen poor gas reservoir in order to establish an oxygen concentration within the enclosed volume which is below the second oxygen concentration level and above the third oxygen concentration level, and detaching the oxygen poor gas reservoir from the enclosed volume.

14. A product providing a system according to claim 1 for the purpose of reduced scarring during the wound healing process.

\* \* \* \* \*